(12) United States Patent
Steemers et al.

(10) Patent No.: US 12,297,565 B2
(45) Date of Patent: May 13, 2025

(54) METHODS AND MEANS FOR PREPARING A LIBRARY FOR SEQUENCING

(71) Applicant: ILLUMINA, INC., San Diego, CA (US)

(72) Inventors: Frank J. Steemers, Encinitas, CA (US); Dmitry K. Pokholok, San Diego, CA (US); Lena Christiansen, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 831 days.

(21) Appl. No.: 17/250,846

(22) PCT Filed: Dec. 13, 2019

(86) PCT No.: PCT/US2019/066272
§ 371 (c)(1),
(2) Date: Mar. 11, 2021

(87) PCT Pub. No.: WO2020/131626
PCT Pub. Date: Jun. 25, 2020

(65) Prior Publication Data
US 2022/0195507 A1    Jun. 23, 2022

Related U.S. Application Data

(60) Provisional application No. 62/780,812, filed on Dec. 17, 2018.

(51) Int. Cl.
| | |
|---|---|
| *C40B 50/06* | (2006.01) |
| *C12N 15/10* | (2006.01) |
| *C12Q 1/6848* | (2018.01) |
| *C12Q 1/6874* | (2018.01) |
| *C12Q 1/6876* | (2018.01) |

(52) U.S. Cl.
CPC .......... *C40B 50/06* (2013.01); *C12N 15/1065* (2013.01); *C12Q 1/6848* (2013.01); *C12Q 1/6874* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 5,925,545 | A | 7/1999 | Reznikoff et al. |
| 5,965,443 | A | 10/1999 | Reznikoff et al. |
| (Continued) | | | |

FOREIGN PATENT DOCUMENTS

| | | |
|---|---|---|
| CN | 1749417 | 3/2006 |
| CN | 101641449 | 2/2010 |
| (Continued) | | |

OTHER PUBLICATIONS

Appleby et al., 2009, New technologies for ultra-high throughput genotyping in plants, Methods Mol Biol., 513:19-39.
(Continued)

*Primary Examiner* — Christian C Boesen
(74) *Attorney, Agent, or Firm* — Illumina, Inc.

(57) ABSTRACT

Embodiments of systems, methods, and compositions provided herein relate to assays for selectively controlling enzymatic reactions. Some embodiments relate to methods of inhibiting, reducing, or eliminating secondary DNA (such as mitochondrial DNA) sequencing reads from open chromatic sequencing, whole genome sequencing, or targeted sequencing.

18 Claims, 7 Drawing Sheets
Specification includes a Sequence Listing.

(56) References Cited

U.S. PATENT DOCUMENTS

| | | | |
|---|---|---|---|
| 7,083,980 | B2 | 8/2006 | Reznikoff et al. |
| 7,608,434 | B2 | 10/2009 | Reznikoff et al. |
| 2002/0090628 | A1 | 7/2002 | Gray et al. |
| 2012/0258892 | A1 | 10/2012 | Wang |
| 2012/0301925 | A1 | 11/2012 | Belyaev |
| 2013/0023423 | A1 | 1/2013 | Kavanagh et al. |
| 2013/0143774 | A1 | 6/2013 | Actis et al. |
| 2014/0242577 | A1 | 8/2014 | Peter |
| 2014/0356877 | A1 | 12/2014 | Krishnan et al. |
| 2017/0254805 | A1 | 9/2017 | Lee et al. |
| 2018/0335424 | A1 | 11/2018 | Chen et al. |

FOREIGN PATENT DOCUMENTS

| | | |
|---|---|---|
| CN | 102732629 | 10/2012 |
| CN | 103602735 | 2/2014 |
| CN | 103710323 | 4/2014 |
| CN | 104395481 | 3/2015 |
| CN | 104508060 | 4/2015 |
| CN | 104968805 | 10/2015 |
| CN | 105018548 | 11/2015 |
| CN | 105339503 | 2/2016 |
| CN | 105463090 | 4/2016 |
| CN | 105658812 | 6/2016 |
| CN | 105683379 | 6/2016 |
| CN | 105779437 | 7/2016 |
| CN | 106414765 | 2/2017 |
| CN | 106459967 | 2/2017 |
| CN | 106520917 | 3/2017 |
| CN | 106661561 | 5/2017 |
| CN | 106701993 | 5/2017 |
| CN | 106715693 | 5/2017 |
| CN | 106754811 | 5/2017 |
| CN | 106755454 | 5/2017 |
| CN | 107794258 | 3/2018 |
| CN | 108103174 | 6/2018 |
| CN | 108350497 | 7/2018 |
| CN | 108368540 | 8/2018 |
| CN | 108866155 | 11/2018 |
| EP | 3 091 026 | 11/2016 |
| EP | 3 409 789 | 12/2018 |
| GB | 0603190 | 2/2006 |
| GB | 201704402 | 5/2017 |
| JP | 2014-521354 | 8/2014 |
| RU | 2609630 C2 | 2/2017 |
| WO | WO 95/23875 | 9/1995 |
| WO | WO 01/009363 | 2/2001 |
| WO | WO 05/040425 | 5/2005 |
| WO | WO 06/133054 | 12/2006 |
| WO | WO 07/093816 | 8/2007 |
| WO | WO 10/048605 | 4/2010 |
| WO | WO 12/003374 | 1/2012 |
| WO | WO 15/157611 | 10/2015 |
| WO | WO 15/160895 | 10/2015 |
| WO | WO 15/196141 | 12/2015 |
| WO | WO 16/003814 | 1/2016 |
| WO | WO 17/125565 | 7/2017 |
| WO | WO 17/156336 | 9/2017 |
| WO | WO 18/172726 | 9/2018 |
| WO | WO 18/195091 | 10/2018 |
| WO | WO 2018/218226 A1 | 11/2018 |
| WO | WO 18/226708 | 12/2018 |

OTHER PUBLICATIONS

Boeke et al., 1989, Transcription and reverse transcription of retrotransposons, Ann. Rev. Microbiol. 43:403-434.

Brown et al., Apr. 1989, Retroviral integration: structure of the initial covalent product and its precursor, and a role for the viral IN protein, Proc. Natl. Acad. Sci. USA, 86:2525-2529.

Colegio et al., Apr. 2001, In vitro transposition system for efficient generation of random mutants of campylobacter jejuni, J. Bacteriol., 183:2384-2388.

Craig, 1996, Transposon Tn7, Curr. Top. Microbiol. Immunol., 204:27-48.

Craig, Mar. 15, 1996, V(D)J recombination and transposition: closer than expected, Science, 271:1512.

Devine et al., 1994, Efficient integration of artificial transposons into plasmid targets in vitro: a useful tool for DNA mapping, sequencing and genetic analysis, Nucleic Acids Res., 22(18):3765-3772.

Fox et al. 2009, Applications of ultra-high-throughput sequencing, Methods Mol Biol., 553:79-108.

Gloor, 2004, Gene targeting in *Drosophila*, Methods Mol. Biol., 260:97-114.

Goryshin et al., Mar. 27, 1998, Tn5 in vitro transposition, J. Biol. Chem. 273:7367-7374.

Ichikawa et al., Nov. 5, 1990, In vitro transposition of Transposon Tn3*, J. Biol. Chem., 265:18829-18832.

Imelfort et al., 2009, De novo sequencing of plant genomes using second-generation technologies, Brief Bioinform, 10(6):609-618.

Kirby et al., 2002, Cryptic plasmids of *Mycobacterium avium*: Tn552 to the rescue, Mol. Microbiol., 43(1):173-186.

Kleckner et al., 1996, Tn10 and IS10 transposition and chromosome rearrangements: mechanism and regulation in vivo and in vitro, Curr. Top. Microbiol. Immunol., 204:49-82.

Lampe et al., 1996, A purified mariner transposase is sufficient to mediate transposition in vitro, EMBO J., 15:5470-5479.

Margulies et al., Sep. 15, 20025, Genome sequencing in open microfabricated high density picoliter reactors, Nature, 437:376-80.

Mizuuchi, Dec. 1983, In vitro transposition of bacteriophage mu: a biochemical approach to a novel replication reaction, Cell, 35:785-794.

Morozova et al., 2008, Applications of next-generation sequencing technologies in functional genomics, Genomics, 92:255-64.

Ohtsubo 1996, Bacterial insertion sequences, Curr. Top. Microbiol. Immunol. 204:1-26.

Plasterk, 1996, The Tc1/mariner transposon family, Curr. Top. Microbiol. Immunol., 204:125-143.

Reznikoff et al., 1999, Tn5: a molecular window on transposition, Biochem. Biophys. Res. Commun., 266:729-734.

Ronaghi et al., 1996, Real-time DNA sequencing using detection of pyrophosphate release, Analytical Biochemistry, 242:84-89.

Savilahti et al., 1995, The phage mu transpososome core: DNA requirements for assembly and function, EMBO J., 14:4893-4903.

Shendure et al., 2005, Accurate multiplex polony sequencing of an evolved bacterial genome, Science, 309:1728-1732.

Wilson et al., 2007, New transposon delivery plasmids for insertional mutagenesis in bacillus anthracis, J. Microbiol. Methods, 71:332-335.

Zhang et al., Oct. 2009, A novel mechanism of transposon-mediate gene activation, PLoS Genet. 5(10):e1000689.

Montefiori et al., "Reducing mitochondrial reads in ATAC-seq using CRISPR/Cas9", Scientific Reports, vol. 7, No. 1, Dec. 26, 2017.

International search report and written opinion issued in application No. PCT/US2019/066272, dated Feb. 25, 2020.

Notice of reasons for rejection dated Oct. 24, 2023 in Japanese patent application No. 2021-514960.

Office action of the substantive examination stage dated Sep. 25, 2023 in Russian patent application No. 2021108003/10(017265).

METHODS AND MEANS FOR PREPARING A LIBRARY FOR SEQUENCING

FIELD

Systems, methods, and compositions provided herein relate to assays for selectively controlling enzymatic reactions. Specifically, aspects disclosed herein relate to methods of inhibiting, reducing, or eliminating secondary DNA sequencing reads from open chromatic sequencing, whole genome sequencing, or targeted sequencing.

BACKGROUND

Enzymes are useful tools in molecular biology and genomics as they can perform a diverse number of steps in a wide application space ranging from genome editing, genomics assays, sequencing, pharmaceutical applications, and diagnostics. Natural and engineered enzymes have experienced an explosion of applications and development throughout the last decade. A strong focus has been specificity and efficiency with the main focus on improving the enzyme system. However, enzymatic systems display off-target effects, causing difficulty in analyzing results.

SUMMARY

The present disclosure is related to systems, methods, and compositions for selectively controlling enzymatic reactions by tagging confounding substrates, which prevents an enzymes ability to interact with the substrate, and thus reducing or eliminating noise or error that would typically be present in the enzymatic reaction.

Some embodiments provided herein relate to nucleic acid libraries comprising primary sequencing reads obtained from sequencing, such as sequencing reads obtained from an assay for transposase-accessible chromatin sequencing (ATAC-seq) for nuclear DNA. In some embodiments, the nucleic acid libraries include sequencing reads from an assay for whole genome sequencing or chromosomal DNA. In some embodiments, the nucleic acid libraries do not include or have reduced representation of secondary sequencing reads, such as from mitochondrial DNA (mtDNA). In some embodiments, the nucleic acid libraries relate to bacterial DNA, plasmids, or extrachromosomal DNA.

Some embodiments provided herein relate to methods of sequencing a nucleic acid without sequencing or with reduced sequencing of secondary nucleic acids. In some embodiments, the methods include providing a sample comprising a nucleic acid, contacting the sample with a DNA-binding molecule, contacting the sample with an insertional enzyme complex to produce tagged nucleic acid fragments, and sequencing the tagged nucleic acid fragments to produce sequence reads.

Some embodiments provided herein relate to methods of inhibiting, eliminating, or reducing a secondary DNA sequencing read, such as mitochondrial DNA (mtDNA) sequencing reads. In some embodiments, the methods include providing a sample comprising secondary nucleic acids and primary nucleic acids, contacting the sample with a DNA-binding molecule that preferentially binds the secondary nucleic acids, such as mtDNA, and performing DNA transposition on open chromatin, wherein the secondary nucleic acids are not transposed or are transposed with reduced efficiency.

BRIEF DESCRIPTION OF THE DRAWINGS

FIG. 3A depicts Hoechst and SYBR Gold staining, FIG. 3B depicts Sytox Orange and Pico Green staining, and FIG. 3C depicts Qubit staining or no staining. High molecular weight DNA products are indicative of inefficient transposition. Inhibition is observed in both SYBR Gold and Sytox Orange at greater than 100 µM concentrations.

DETAILED DESCRIPTION

Figure 1:
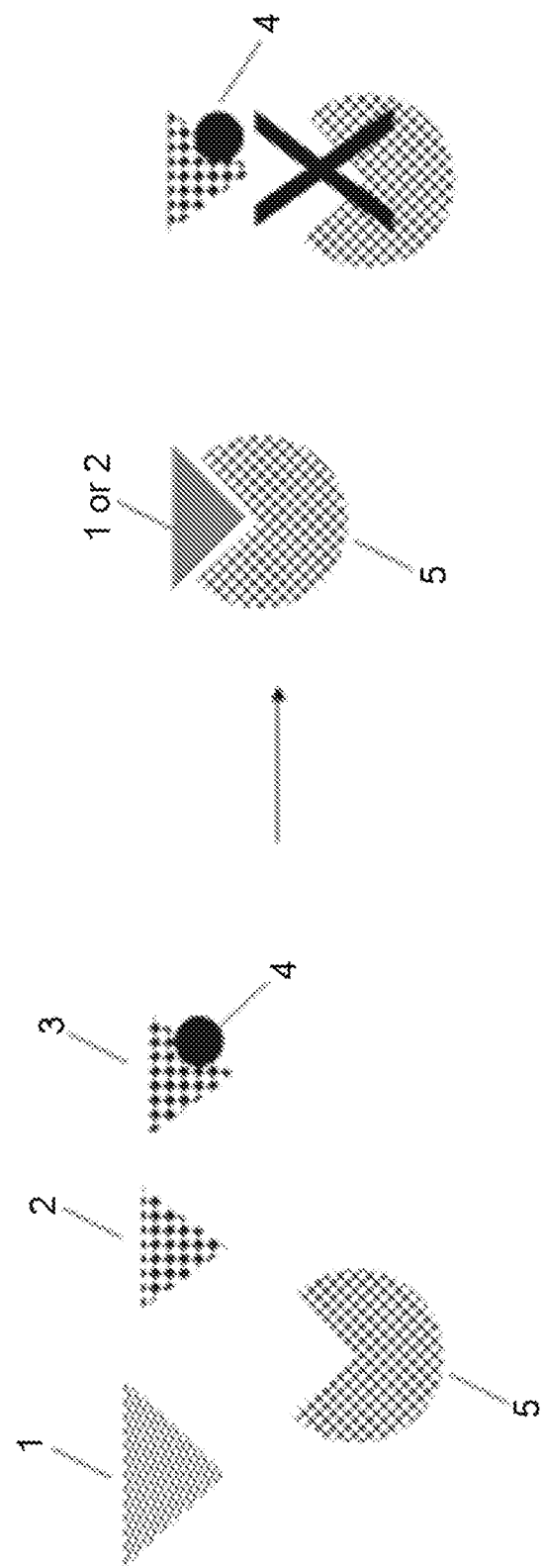
FIG. 1 is a schematic that illustrates modification of a target to control specificity of an enzyme. Substrates (1, 2, or 3) are all substrates for enzyme (5). Substrate 3 modified by 4 is not a substrate for enzyme (5), due to the modification (4). Modification (4) can be a DNA stain, affinity tag, molecule, ligand, enzyme, peptide, or other modification.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments of the systems, methods, and compositions provided herein relate to controlling enzymatic reactions by preventing an enzyme from binding to confounding substrates, such as a substrate that the enzyme would normally bind, but which prevents proper analysis of a substrate of interest.

Traditional enzymatic reactions lack specificity necessary for analyzing differences between closely related substrates. For example, enzymes against nucleic acids poorly discriminate between various types of nucleic acids, such as mitochondrial DNA (mtDNA) compared to nuclear DNA. The result is traditional enzymatic reactions provide results for both the target analyte as well as off-target analytes, thereby confounding the results, and leading time, cost, and complexity in analysis. However, in many applications, it is desirable to control the selectivity of enzymatic reactions.

One embodiment is a system and method to reduce, inhibit, or eliminate undesired targets, thereby specifically targeting only the analyte of interest. FIG. 1 schematically depicts the concept of enzyme to substrate binding. In FIG. 1, an enzyme 5 is capable of recognizing and binding different substrates 1, 2, and 3, which are then catalyzed enzymatically by the enzyme. However, substrate 3 is modified by modification 4, such that the enzyme 5 does not recognize and bind substrate 3. FIG. 1 depicts the methods and systems in a generic schematic. In embodiments provided herein, the concept is described in terms of a transposase and nucleic acids, specifically in terms of a primary DNA sequencing read (which is a sequencing read of a DNA of interest, including, for example, nuclear DNA) and a secondary DNA sequencing read (which is a sequencing read of an undesirable DNA, including, for example, mitochondrial DNA (mtDNA), or extrachromosomal DNA). However, it is to be understood that the general methods and systems are applicable to other enzyme/substrate systems. Embodiments of the systems, methods, and compositions improve the specificity of enzymatic reactions, thereby improving enzymatic analysis by reducing off-target effects.

For example, this approach can be applied so that specific stains, or DNA binding molecules in general, can be brought to certain targets using well-known affinity tags. These affinity tags can include antibody conjugates and DNA hybridization probes to block undesired enzymatic activity. By specifically blocking certain types of DNA, but not others, one can decrease the undesirable off-target effects found with certain enzymes. Alternatively, specific affinity tags ("blockers") can be used to bring enzymes to specific targets. Such applications may include blocking off-target activity of widely used proteins, such as CRISPR enzymes.

As used herein, DNA binding molecule refers to a molecule that can bind to all DNA, but that has preferential access to certain DNA due to accessibility determined by a variety of factors, including, for example, size, charge, or hydrophobicity of the DNA binding molecule. The result is that certain DNA types are preferentially blocked, whereas others are accessible to enzyme systems that can generate sequencing libraries. Thus, in some embodiments, differential access to DNA is allowed in certain types of DNA by binding with the DNA binding molecule, such that the DNA is rendered less active towards enzymatic reactions. For example, a DNA stain does not enter the nucleus, but may enter mtDNA, thereby preferentially blocking mtDNA.

Some embodiments provided herein relate to a nucleic acid library. In some embodiments, the nucleic acid library includes sequencing reads obtained from assay for transposase-accessible chromatin sequencing (ATAC-seq) for a primary DNA (such as nuclear DNA) but does not include, or includes reduced amounts of, sequencing reads from off-target nucleic acids (a secondary DNA), such as mtDNA. In some embodiments, the sequencing reads from the secondary DNA are eliminated, reduced, or inhibited due to DNA-binding molecules that preferentially bind secondary DNA. In some embodiments, the DNA-binding molecule comprises a DNA dye, an affinity tag, a ligand, an enzyme, peptide, or a biomolecule. In some embodiments, the DNA dye comprises Hoechst dye, SYBR Gold, Sytox Orange, Pico Green, or Qubit. In some embodiments, the nucleic acid library is generated from a population of cells, a single cell, a population of cell nuclei, or a single cell nucleus.

As used herein "nucleic acid library" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate.

An array can refer to a population of different microfeatures, such as microfeatures comprising polynucleotides, which are associated or attached with a surface such that the different microfeatures can be differentiated from each other according to relative location. An individual feature of an array can include a single copy of a microfeature or multiple copies of the microfeature can be present as a population of microfeatures at an individual feature of the array. The population of microfeatures at each feature typically is homogenous, having a single species of microfeature. Thus, multiple copies of a single nucleic acid sequence can be present at a feature, for example, on multiple nucleic acid molecules having the same sequence.

In some embodiments, a heterogeneous population of microfeatures can be present at a feature. In some embodiments, a feature can include only a single microfeature species. In some embodiments, a feature can include a plurality of different microfeature species, such as a mixture of nucleic acids having different sequences. Neighboring features of an array can be discrete from one another. Features can be adjacent to each other or separated by a gap. In embodiments where features are spaced apart, neighboring sites can be separated, for example, by a distance of less than 100 µm, 50 µm, 10 µm, 5 µm, 1 µm, 0.5 µm, 100 nm, 50 nm, 10 nm, 5 nm, 1 nm, 0.5 nm or any distance within a range of any two of the foregoing distances. The layout of features on an array can also be understood in terms of center-to-center distances between neighboring features. An array useful in the invention can have neighboring features with center-to-center spacing of less than about 100 µm, 50 µm, 10 µm, 5 µm, 1 µm, 0.5 µm, 100 nm, 50 nm, 10 nm, 5 nm, 1 nm, 0.5 nm or any distance within a range of any two of the foregoing distances. In some embodiments, the distance values described herein can represent an average distance between neighboring features of an array. As such, not all neighboring features need to fall in the specified range unless specifically indicated to the contrary, for example, by a specific statement that the distance constitutes a threshold distance between all neighboring features of an array. Embodiments can include arrays having features at a variety of densities. Example ranges of densities for certain embodiments include from about 10,000,000 features/cm$^2$ to about 2,000,000,000 features/cm$^2$; from about 100,000,000 features/cm$^2$ to about 1,000,000,000 features/cm$^2$; from about 100,000 features/cm$^2$ to about 10,000,000 features/cm$^2$; from about 1,000,000 features/cm$^2$ to about 5,000,000 features/cm$^2$; from about 10,000 features/cm$^2$ to about 100,000 features/cm$^2$; from about 20,000 features/cm$^2$ to about 50,000 features/cm$^2$; from about 1,000 features/cm$^2$ to about 5,000 features/cm$^2$, or any density within a range of any two of the foregoing densities.

As used herein, "surface" can refer to a part of a substrate or support structure that is accessible to contact with reagents, beads or analytes. The surface can be substantially flat or planar. Alternatively, the surface can be rounded or contoured. Example contours that can be included on a surface are wells, depressions, pillars, ridges, channels or the like. Example materials that can be used as a substrate or support structure include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or sepharose; nylon; nitrocellulose; resin; silica or silica-based materials including silicon and modified silicon; carbon-fiber; metal; inorganic glass; optical fiber bundle, or a variety of other polymers. A single material or mixture of several different materials can form a surface useful in the invention. In some embodiments, a surface comprises wells.

As used herein, "bead" can refer to a small body made of a rigid or semi-rigid material. The body can have a shape characterized, for example, as a sphere, oval, microsphere, or other recognized particle shape whether having regular or irregular dimensions. Example materials that are useful for beads include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon; carbon-fiber; metal; inorganic glass; optical fiber bundle, or a variety of other polymers. Example beads include controlled pore glass beads, paramagnetic beads, thoria sol, Sepharose beads, nanocrystals and others known in the art. Beads can be made of biological or non-biological materials. Magnetic beads are particularly useful due to the ease of manipulation of magnetic beads using magnets. Beads used in certain embodiments can have a diameter, width or length from 0.1 μm to 100 μm. Bead size can be selected to have a reduced size, and hence have increased density, whilst maintaining sufficient signal to analyze the features.

As used herein, "hybridization", "hybridizing" or grammatical equivalent thereof, can refer to a reaction in which one or more polynucleotides react to form a complex that is formed at least in part via hydrogen bonding between the bases of the nucleotide residues. The hydrogen bonding can occur by Watson-Crick base pairing, Hoogstein binding, or in any other sequence-specific manner. The complex can have two strands forming a duplex structure, three or more strands forming a multi-stranded complex, a single self-hybridizing strand, or any combination of thereof. The strands can also be cross-linked or otherwise joined by forces in addition to hydrogen bonding.

As used herein, "extending", "extension" or any grammatical equivalents thereof can refer to the addition of dNTPs to a primer, polynucleotide or other nucleic acid molecule by an extension enzyme such as a polymerase. For example, in some embodiments disclosed herein, the resulting extended primer includes sequence information of a nucleic acid. While some embodiments are discussed as performing extension using a polymerase such as a DNA polymerase, or a reverse transcriptase, extension can be performed in any other manner well known in the art. For example, extension can be performed by ligating oligonucleotides together, such as oligonucleotides that have hybridized to a strand of interest.

As used herein, "ligation" or "ligating" or other grammatical equivalents thereof can refer to the joining of two nucleotide strands by a phosphodiester bond. Ligation may include chemical ligation. Such a reaction can be catalyzed by a ligase. A ligase refers to a class of enzymes that catalyzes this reaction with the hydrolysis of ATP or a similar triphosphate.

As used herein "polynucleotide" and "nucleic acid", may be used interchangeably, and can refer to a polymeric form of nucleotides of any length, either ribonucleotides or deoxyribonucleotides. Thus, these terms include single-, double-, or multi-stranded DNA or RNA. Examples of polynucleotides include a gene or gene fragment, whole genomic DNA, genomic DNA, epigenomic, genomic DNA fragment, mitochondrial DNA (mtDNA), nuclear DNA, ribosomal DNA, exon, intron, messenger RNA (mRNA), regulatory RNA, transfer RNA, ribosomal RNA, non-coding RNA (ncRNA) such as PIWI-interacting RNA (piRNA), small interfering RNA (siRNA), and long non-coding RNA (lncRNA), small hairpin (shRNA), small nuclear RNA (snRNA), micro RNA (miRNA), small nucleolar RNA (snoRNA) and viral RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can include modified nucleotides, such as methylated nucleotides and nucleotide analogs including nucleotides with non-natural bases, nucleotides with modified natural bases such as aza- or deaza-purines. A polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. The term "nucleic acid sequence" can refer to the alphabetical representation of a polynucleotide or any nucleic acid molecule, including natural and non-natural bases. Additionally, DNA can contain an unnatural base pair(s) (UBP). UBP is a designed subunit (or nucleobase) of DNA that is created in a laboratory and does not occur in nature.

As used herein, a primary nucleic acid is a nucleic acid of interest. In some embodiments, the primary nucleic acid is nuclear DNA. The primary nucleic acid can be any nucleic acid that is desired to be analyzed in a sample. As used herein, a secondary nucleic acid is a nucleic acid that is found in a sample, but that is not the nucleic acid of interest, and thus is an interference in the context of analysis of a nucleic acid of interest. In some embodiments, the secondary nucleic acid is mitochondrial DNA (mtDNA) or extrachromosomal DNA. The secondary nucleic acid can be any nucleic acid that is found in a sample but that is not the object of analysis, and that is desirable to inhibit, reduce, or eliminate from analysis in order to more efficiently and accurately analyze the nucleic acid of interest. Extrachromosomal DNA is any DNA that is found outside of the nucleus of a cell. It is also referred to as extranuclear DNA or cytoplasmic DNA.

A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole). In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acyclic 5-nitroindole, 4-nitropyrazole, 4-nitroimidazole and 3-nitropyrrole. Promiscuous bases that can base pair with at least two, three, four or more types of bases can be used.

An assay for transposase accessible chromatic using sequencing (ATAC-seq) refers to a rapid and sensitive method of integrative epigenomic analysis. ATAC-seq captures open chromatin sites and reveals interplay between genomic locations of open chromatin, DNA binding proteins, individual nucleosomes, and higher-order compaction at regulatory regions with nucleotide resolution. Classes of DNA binding factor that strictly avoid, can tolerate, or tend to overlap with nucleosomes have been discovered. Using ATAC-seq, the serial daily epigenomes of resting human T cells was measured and evaluated from a pro band via standard blood draws, demonstrating the feasibility of reading personal epigenomes in clinical timescales for monitoring health and disease. More specifically, ATAC-seq may be performed by treating chromatin from a single cell with an insertional enzyme complex to produce tagged fragments of genomic DNA. In this step, the chromatin is tagmented (for example, fragmented and tagged in the same reaction) using an insertional enzyme such as Tn5 or MuA that cleaves the genomic DNA in open regions in the chromatin and adds adaptors to both ends of the fragments. In some embodiments, the application is whole genome sequencing or epigenomic profiling.

Whole genome sequencing (WGS) refers to a method of reading the genome by many multiples such as in 10×, 20×, and 40× formats for whole genome sequencing by next generation sequencing. Targeted sequencing refers to methods or assays that determine the DNA sequence of chosen DNA loci or genes in a sample, for example sequencing a chosen group of cancer-related genes.

In some cases, the conditions may be adjusted to obtain a desirable level of insertion in the chromatin (e.g., an insertion that occurs, on average, every 50 to 200 base pairs in open regions). The chromatin used in the method may be made by any suitable method. In some embodiments, nuclei may be isolated, lysed, and the chromatin may be further purified, e.g., from the nuclear envelope. In other embodiments, the chromatin may be isolated by contacting isolated nuclei with the reaction buffer. In these embodiments, the isolated nuclei may lyse when it makes contact with the reaction buffer (which comprises insertional enzyme complexes and other necessary reagents), which allows the insertional enzyme complexes access to the chromatin. In these embodiments, the method may comprise isolating nuclei from a population of cells; and combining the isolated nuclei with the transposase and adaptors, wherein the combining results in both lysis of the nuclei to release said chromatin and production of the adaptor-tagged fragments of genomic DNA. The chromatin does not require cross-linking as in other methods (e.g., ChIP-SEQ methods). In some embodiments, enzymatic reactions occur directly from cells.

After the chromatin has been fragmented and tagged to produce tagged fragments of genomic DNA, at least some of the adaptor tagged fragments are sequenced to produce a plurality of sequence reads. The fragments may be sequenced using any suitable method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova et al. (Genomics. 2008 92:255-64), which are incorporated by reference herein for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. Methods of performing ATAC-seq are set forth in PCT Application No. PCT/US2014/038825, which is incorporated by reference herein in its entirety.

The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

In some embodiments, the methods described herein further include further analyzing the target nucleic acid of interest. Analyzing may include, for example, DNA analysis, RNA analysis, protein analysis, tagmentation, nucleic acid amplification, nucleic acid sequencing, nucleic acid library preparation, contiguity-preserving transposition (CPT-seq), single cell combinatorial indexed sequencing (SCI-seq), or single cell genome amplification, whole genome sequencing from single cells or from a population of cells, epigenomics, or any combination thereof.

DNA analysis refers to any technique used to amplify, sequence, or otherwise analyze DNA. DNA amplification can be accomplished using PCR techniques. DNA analysis may also comprise non-targeted, non-PCR based DNA sequencing (e.g., metagenomics) techniques. As a non-limiting example, DNA analysis may include sequencing the hyper-variable region of the 16S rDNA (ribosomal DNA) and using the sequencing for species identification via DNA. In some embodiments, the DNA can include purified DNA.

RNA analysis refers to any technique used to amplify, sequence, or otherwise analyze RNA. The same techniques used to analyze DNA can be used to amplify and sequence RNA. RNA, which is less stable than DNA is the translation of DNA in response to a stimuli. Therefore, RNA analysis may provide a more accurate picture of the metabolically active members of the community and may be used to provide information about the community function of organisms in a sample. Nucleic acid sequencing refers to use of sequencing to determine the order of nucleotides in a sequence of a nucleic acid molecule, such as DNA or RNA. In some embodiments, DNA analysis can also include methods that do not require or use amplification.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing" or "NGS" generally refers to high throughput sequencing technologies, including, but not limited to, massively parallel signature sequencing, high throughput sequencing, sequencing by ligation (e.g., SOLiD sequencing), proton ion semiconductor sequencing, DNA nanoball sequencing, single molecule sequencing, and nanopore sequencing and may refer to the parallelized sequencing-by-synthesis or sequencing-by-ligation platforms currently employed by Illumina, Life Technologies, or Roche, etc. Next-generation sequencing methods may also include nanopore sequencing methods or electronic-detection based methods such as Ion Torrent technology commercialized by Life Technologies or single molecule fluorescence-based method commercialized by Pacific Biosciences and/or BGI Microfluidics.

Exemplary sequencing techniques include targeted sequencing, single molecule real-time sequencing, electron microscopy-based sequencing, transistor-mediated sequencing, direct sequencing, random shotgun sequencing, Sanger dideoxy termination sequencing, targeted sequencing, exon sequencing, whole-genome sequencing, sequencing by hybridization (e.g., in an array such as a microarray), pyrosequencing, capillary electrophoresis, gel electrophoresis, duplex sequencing, cycle sequencing, single-base extension sequencing, solid-phase sequencing, high-throughput sequencing, massively parallel shotgun sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, ion semiconductor sequencing, nanoball sequencing, nanopore sequencing, 454 sequencing, Solexa Genome Analyzer sequencing, miSeq (Illumina), HiSeq 2000 (Illumina), HiSeq 2500 (Illumina), Illumina Genome Analyzer (Illumina), Ion Torrent PGM™ (Life Technologies), MinION™ (Oxford Nanopore Technologies), real-time SMRT™ technology (Pacific Biosciences), the Probe-Anchor Ligation (cPAL™) (Complete Genomics/BGI), SOLiD® sequencing, MS-PET sequencing, mass spectrometry, and a combination thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 373OxI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique. In certain embodiments, sequencing comprises whole genome sequencing. In certain embodiments, sequencing comprises massively parallel sequencing (e.g., massively parallel shotgun sequencing). In alternative embodiments, sequencing comprises targeted sequencing.

Protein analysis refers to the study of proteins, and may include proteomic analysis, determination of post-translational modification of proteins of interest, determination of protein expression levels, or determination of protein interactions with other molecules, including with other proteins or with nucleic acids.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

Contiguity-preserving transposition sequencing (CPT-seq) refers to a method of sequencing while preserving contiguity information by the use of transposase to maintain the association of template nucleic acid fragments adjacent in the target nucleic acid. For example, CPT may be carried out on a nucleic acid, such as on DNA. The CPT-nucleic acid can be captured by hybridization of complimentary oligonucleotides having unique indexes or barcodes and immobilized on a solid support. In some embodiments, the oligonucleotide immobilized on the solid support may further comprise primer-binding sites, unique molecular indices, in addition to barcodes. Advantageously, such use of transposomes to maintain physical proximity of fragmented nucleic acids increases the likelihood that fragmented nucleic acids from the same original molecule, e.g., chromosome, will receive the same unique barcode and index information from the oligonucleotides immobilized on a solid support. This will result in a contiguously-linked sequencing library with unique barcodes. The contiguously-linked sequencing library can be sequenced to derive contiguous sequence information.

As used herein the term "contiguity information" refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived.

Therefore, according to the embodiments described herein, methods of capturing contiguity information may be accomplished by short range contiguity methods to determine adjacent spatial relationships, mid-range contiguity methods to determine compartmental spatial relationships, or long range contiguity methods to determine distance spatial relationships. These methods facilitate the accuracy and quality of DNA sequence assembly or mapping, and may be used with any sequencing method, such as those described herein.

Contiguity information includes the relative genomic origins or coordinates of the individual sequence reads as they relate to the spatial relationship between the two or more DNA fragments from which the individual sequence reads were derived. In some embodiments, contiguity information includes sequence information from non-overlapping sequence reads.

In some embodiments, the contiguity information of a target nucleic acid sequence is indicative of haplotype information. In some embodiments, the contiguity information of a target nucleic acid sequence is indicative of genomic variants.

Single cell combinatorial indexed sequencing (SCI-seq) is a sequencing technique for simultaneously generating thousands of single cell libraries for a variety of analyses, including, for example, whole genome, methylation, RNA, simultaneous DNA and RNA, or Hi-C, or other analyses of libraries or any combination thereof.

A transposition reaction is a reaction wherein one or more transposons are inserted into target nucleic acids at random sites or almost random sites. Components in a transposition reaction include a transposase (or other enzyme capable of fragmenting and tagging a nucleic acid as described herein, such as an integrase) and a transposon element that includes a double-stranded transposon end sequence that binds to the transposase (or other enzyme as described herein), and an adaptor sequence attached to one of the two transposon end sequences. One strand of the double-stranded transposon end sequence is transferred to one strand of the target nucleic acid and the complementary transposon end sequence strand is not (a non-transferred transposon sequence). The adaptor sequence can include one or more functional sequences or components (e.g., primer sequences, anchor sequences, universal sequences, spacer regions, or index tag sequences) as needed or desired.

Transposon based technology can be utilized for fragmenting DNA, for example, as exemplified in the workflow for NEXTERA' XT and FLEX DNA sample preparation kits (Illumina, Inc.), wherein target nucleic acids, such as genomic DNA, are treated with transposome complexes that simultaneously fragment and tag (tagmentation) the target, thereby creating a population of fragmented nucleic acid molecules tagged with unique adaptor sequences at the ends of the fragments.

An insertional enzyme complex as used herein, refers to a complex comprising an insertional enzyme and two adaptor molecules (the "transposon tags") that are combined with polynucleotides to fragment and add adaptors to the polynucleotides. Thus, an insertional enzyme complex may be a "transposome complex" is comprised of at least one transposase (or other enzyme as described herein) and a transposon recognition sequence. In some such systems, the transposase binds to a transposon recognition sequence to form a functional complex that is capable of catalyzing a transposition reaction. In some aspects, the transposon recognition sequence is a double-stranded transposon end sequence. The transposase binds to a transposase recognition site in a target nucleic acid and inserts the transposon recognition sequence into a target nucleic acid. In some such insertion events, one strand of the transposon recognition sequence (or end sequence) is transferred into the target nucleic acid, resulting in a cleavage event. Exemplary transposition procedures and systems that can be readily adapted for use with the transposases of the present disclosure are described, for example, in PCT Publ. No. WO10/048605, U.S. Pat. Publ. No. 2012/0301925, U.S. Pat. Publ. No. 2012/13470087, or U.S. Pat. Publ. No. 2013/0143774, each of which is incorporated herein by reference in its entirety.

Exemplary transposases that can be used with certain embodiments provided herein include (or are encoded by): Tn5 transposase (see Reznikoff et al., Biochem. Biophys. Res. Commun. 1999, 266, 729-734), Sleeping Beauty (SB) transposase, *Vibrio harveyi* (transposase characterized by Agilent and used in SureSelect QXT product), MuA transposase and a Mu transposase recognition site comprising R1 and R2 end sequences (Mizuuchi, K., Cell, 35: 785, 1983; Savilahti, H, et al., EMBO J., 14:4893, 1995), *Staphylococcus aureus* Tn552 (Colegio, O. et al., J. Bacteriol., 183: 2384-8, 2001; Kirby, C. et al., Mol. Microbiol., 43:173-86, 2002), Ty1 (Devine & Boeke, Nucleic Acids Res., 22:3765-72, 1994 and PCT Publ. No. WO95/23875), Transposon Tn7 (Craig, N. L., Science, 271:1512, 1996; Craig, N. L., Curr. Top. Microbiol. Immunol., 204:27-48, 1996), Tn/O and IS10 (Kleckner N. et al., Curr. Top. Microbiol. Immunol., 204: 49-82, 1996), Mariner transposase (Lampe, D. J. et al., EMBO J., 15:5470-9, 1996), Tc1 (Plasterk, R. H., Curr. Top. Microbiol. Immunol., 204:125-43, 1996), P Element (Gloor, G. B., Methods Mol. Biol., 260:97-114, 2004), Tn3 (Ichikawa & Ohtsubo, J. Biol. Chem., 265:18829-32, 1990), bacterial insertion sequences (Ohtsubo & Sekine, Curr. Top. Microbiol. Immunol. 204:1-26, 1996), retroviruses (Brown et al., Proc. Natl. Acad. Sci. USA, 86:2525-9, 1989), and retrotransposon of yeast (Boeke & Corces, Ann. Rev. Microbiol. 43:403-34, 1989). More examples include IS5, Tn10, Tn903, IS911, and engineered versions of transposase family enzymes (Zhang et al., (2009) PLoS Genet. 5:e1000689. Epub October 16; Wilson C. et al. (2007) J. Microbiol. Methods 71:332-5), each of the references cited herein with respect to the transposase is incorporated herein by reference in its entirety. The methods described herein could also include combinations of transposases, and not just a single transposase.

In some embodiments, the transposase is a Tn5, MuA, or *Vibrio harveyi* transposase, or an active mutant thereof. In other embodiments, the transposase is a Tn5 transposase or an active mutant thereof. In some embodiments, the Tn5 transposase is a hyperactive Tn5 transposase (see, e.g., Reznikoff et al., PCT Publ. No. WO2001/009363, U.S. Pat. Nos. 5,925,545, 5,965,443, 7,083,980, and 7,608,434, and Goryshin and Reznikoff, J. Biol. Chem. 273:7367, 1998), or an active mutant thereof. In some aspects, the Tn5 transposase is a Tn5 transposase as described in PCT Publ. No. WO2015/160895, which is incorporated herein by reference. In some embodiments, the Tn5 transposase is a fusion protein. In some embodiments, the Tn5 transposase fusion protein comprises a fused elongation factor Ts (Tsf) tag. In some embodiments, the Tn5 transposase is a hyperactive Tn5 transposase comprising mutations at amino acids 54, 56, and 372 relative to the wild type sequence. In some embodiments, the hyperactive Tn5 transposase is a fusion protein, optionally wherein the fused protein is elongation factor Ts (Tsf). In some embodiments, the recognition site is a Tn5-type transposase recognition site (Goryshin and Reznikoff, J. Biol. Chem., 273:7367, 1998). In one embodiment, a transposase recognition site that forms a complex with a hyperactive Tn5 transposase is used (e.g., EZ-Tn5™ Transposase, Epicentre Biotechnologies, Madison, Wis.). In some embodiments, the Tn5 transposase is a wild-type Tn5 transposase.

In any of the embodiments of the methods, compositions, or systems described herein, the transposon includes a transposon end sequence. In some embodiments, the transposon end sequence is a mosaic end (ME) sequence. In some embodiments, DNA is tagged using tagmentation, wherein the DNA is tagged with a tag, and included with the tag is a transposon-specific sequence, such as an ME sequence. Thus, the DNA is differentiated from RNA in the sample based on the transposon-specific sequence.

In any of the embodiments of the methods, compositions, or systems described herein, the transposon includes an adaptor sequence. Adaptor sequences may comprise one or more functional sequences or components selected from the group consisting of primer sequences, anchor sequences, universal sequences, spacer regions, index sequences, capture sequences, barcode sequences, cleavage sequences, sequencing-related sequences, and combinations thereof. In some embodiments, an adaptor sequence comprises a primer sequence. In other embodiments, an adaptor sequence comprises a primer sequence and an index or barcode sequence. A primer sequence may also be a universal sequence. This disclosure is not limited to the type of adaptor sequences that could be used and a skilled artisan will recognize additional sequences that may be of use for library preparation and next generation sequencing. A universal sequence is a region of nucleotide sequence that is common to two or more nucleic acid fragments. Optionally, the two or more nucleic acid fragments also have regions of sequence differences. A universal sequence that may be present in different members of a plurality of nucleic acid fragments can allow for the replication or amplification of multiple different sequences using a single universal primer that is complementary to the universal sequence.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes.

In any of the embodiments, the adaptor sequence or transposon end sequences, including A14-ME, ME, B15-ME, ME', A14, B15, and ME are provided below:

```
                                              (SEQ ID NO: 1)
A14-ME:  5'-TCGTCGGCAGCGTCAGATGTGTATAAGAGACAG-3'

(SEQ ID NO: 2)
B15-ME:  5'-GTCTCGTGGGCTCGGAGATGTGTATAAGAGACAG-3'

(SEQ ID NO: 3)
ME':  5'-phos-CTGTCTCTTATACACATCT-3'

(SEQ ID NO: 4)
A14:  5'-TCGTCGGCAGCGTC-3'

(SEQ ID NO: 5)
B15:  5'-GTCTCGTGGGCTCGG-3'

(SEQ ID NO.: 6)
ME:  AGATGTGTATAAGAGACAG
```

In some embodiments, the primer sequences are includes to prepare the libraries for sequencing. In some embodiments, the primer sequence is a P5 primer sequence or a P7 primer sequence. The P5 and P7 primers are used on the surface of commercial flow cells sold by Illumina, Inc., for sequencing on various Illumina platforms. The primer sequences are described in U.S. Patent Publication No. 2011/0059865 A1, which is incorporated herein by reference in its entirety. Examples of P5 and P7 primers, which may be alkyne terminated at the 5' end, include the following:

```
                                              (SEQ ID NO. 7)
    P5:  AATGATACGGCGACCACCGAGAUCTACAC (SEQ ID NO. 8)
    P7:  CAAGCAGAAGACGGCATACGAG*AT
``` and derivatives or analogues thereof. In some examples, the P7 sequence includes a modified guanine at the G* position, e.g., an 8-oxo-guanine. In other examples, the * indicates that the bond between the G* and the adjacent 3' A is a phosphorothioate bond. In some examples, the P5 and/or P7 primers include unnatural linkers. Optionally, one or both of the P5 and P7 primers can include a poly T tail. The poly T tail is generally located at the 5' end of the sequence shown above, e.g., between the 5' base and a terminal alkyne unit, but in some cases can be located at the 3' end. The poly T sequence can include any number of T nucleotides, for example, from 2 to 20. While the P5 and P7 primers are given as examples, it is to be understood that any suitable primers can be used in the examples presented herein. The index sequences having the primer sequences, including the P5 and P7 primer sequences serve to add P5 and P7 for activating the library for sequencing.

A nucleic acid binding molecule is a molecule that preferentially binds to a nucleic acid, such as to a DNA or RNA. The nucleic acid binding molecule, such as a DNA-binding molecule, may be specific for a certain type of nucleic acid, without binding to other types of nucleic acids. For example, a DNA-binding molecule may bind preferentially to mtDNA, but does not bind, or binds to a lesser extent, to other nucleic acids, such as nuclear DNA. Examples of nucleic acid binding molecules includes a dye or stain, a protein, an enzyme, a biomolecule, an affinity tag, a particle, a fluorescent label, a peptide, a ligand, or other molecule capable of specifically binding to a nucleic acid. Thus, in some examples, the nucleic acid binding molecule is a Hoechst dye, a cyanine dye (including, for example, SYBR dyes, such as SYBR green, SYBR gold, oxazole yellow, thiazole orange, PicoGreen, Safe green), 4',6-diamidino-2-phenylindole (DAPI), or Sytox dyes (including, for example, Sytox green or Sytox orange). Other nucleic acid binding molecules may include, for example, 7-AAD (7-amino-actinomycin D), acridine orange, acridine red, Alexa Fluor 594, Alexa Fluor 610 R-phycoerythrin streptavidin pH 7.2, Alexa Fluor 647 R-phycoerythrin streptavidin pH 7.2, Alexa Fluor 633, Alexa Fluor 647, Alexa Fluor 660, Alexa Fluor 680, Alexa Fluor 700, Alexa Fluor 750, allophycocyanine (APC), BOBO-3-DNA, BOBO-3, Bodipy 650/665-X, Cy5.5, Cy5, DDAO, Draq5, ethidiumbromide, ethidiummonoazide, ethidium homodimer, ethidium homodimer-1 (EthD-1), ethidium homodimer-1-DNA, ethidium homodimer-2, LDS 751, LDS 751 (DNA), LOLO-1, MitoTracker red, Nile blue-EtOH, OliGreen, dsDNA quantitation reagent, POPO-1-DNA, PO-PRO-1-DNA, propidiumiodide (PI), propidiumiodide-DNA, Ribogreen, SYPRO Ruby, SYTO 60, SYTO 61, SYTO 62, SYTO 63, SYTO 64, Texas Red, TO-PRO-1-DNA, TO-PRO-3, TO-PRO-5, TOTO-1-DNA, TOTO-3, YO-PRO-1-DNA, YO-PRO-3, YOYO-1, YOYO-1-DNA and YOYO-3. These nucleic acid binding molecules are exemplary molecules that can be used, and a person of skill in the art will recognize that any nucleic acid binding molecule that discriminates between a target nucleic acid of interest and off-target nucleic acids may be used.

Some embodiments provided herein relate to a method of sequencing a nucleic acid. In some embodiments, the method includes providing a sample comprising a nucleic acid, contacting the sample with a DNA-binding molecule, contacting the sample with an insertional enzyme complex to produce tagged nucleic acid fragments, and sequencing the tagged nucleic acid fragments to produce sequence reads. In some embodiments, the sample is a population of cells, a single cell, a population of cell nuclei, or a single cell nucleus. In some embodiments, the sample comprises mtDNA and nuclear DNA, and wherein the DNA-binding molecule binds to mtDNA but not to nuclear DNA. In some embodiments, the DNA-binding molecule comprises a DNA dye, an affinity tag, a ligand, an enzyme, peptide, or a biomolecule. In some embodiments, the DNA dye comprises Hoechst dye, SYBR Gold, Sytox Orange, Pico Green, or Qubit. In some embodiments, the insertional enzyme complex is a transposome comprising a transposase. In some embodiments, sequencing is performed by ATAC-seq. In some embodiments, ATAC-seq comprises bulk ATAC-seq or single cell ATAC-seq. In some embodiments, the method inhibits, reduces, or eliminates mtDNA sequencing reads. In some embodiments, the nucleic acid binding molecule preferentially binds to a specific DNA sequence or sequences.

Some embodiments provided herein relate to a method of inhibiting, reducing, or eliminating mtDNA sequencing reads. In some embodiments, the method includes providing a sample comprising mtDNA and a nucleic acid of interest, contacting the sample with a DNA-binding molecule that preferentially binds a secondary DNA, such as mtDNA, and performing DNA transposition on open chromatin, wherein the secondary DNA, such as mtDNA is not transposed. In some embodiments, the sample is a population of cells, a single cell, a population of cell nuclei, or a single cell nucleus. In some embodiments, the DNA-binding molecule comprises a DNA dye, an affinity tag, a ligand, an enzyme, peptide, or a biomolecule. In some embodiments, the DNA dye comprises Hoechst dye, SYBR Gold, Sytox Orange, Pico Green, or Qubit. In some embodiments, the DNA transposition is performed using ATAC-seq. In some embodiments, ATAC-seq comprises bulk ATAC-seq or single cell ATAC-seq. In some embodiments, contacting the sample with the DNA-binding molecule blocks transposition into mtDNA. In some embodiments, the nucleic acid of interest comprises nuclear DNA. In some embodiments, the method further includes sequencing nuclear DNA.

As used herein, a sample includes any sample having an analyte of interest. The sample may be a biological sample, such as a biological sample having an analyte of interest, including, for example, whole blood, serum, interstitial fluid, lymph, cerebrospinal fluid, sputum, urine, stool, milk, sweat, tears, umbilical cord, peripheral blood, bone marrow, cells or solid tissue. In some embodiments, the sample is a population of cells, a cell, a population of cell nuclei, or a cell nucleus. The sample may be obtained from a subject, wherein it is desirable to analyze one or more analyte of interest from the subject. As used herein, a "subject" refers to an animal that is the object of treatment, observation, or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

The sample may be a fluid or specimen obtained from an environmental source. For example, the fluid or specimen obtained from the environmental source can be obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, or any combinations thereof. In some embodiments, the sample is a fluid or specimen collected or derived from a cell culture or from a microbe colony.

As used herein, "analyte", "target analyte", "analyte of interest" are used interchangeably and refer to the analyte being measured in the methods and systems disclosed herein. In some embodiments, the analyte may be a biomolecule. Non-limiting examples of biomolecules include macromolecules such as, polynucleotide (e.g., DNA or RNA), proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, proteins tagged with oligonucleotides, or the like. The target analyte may be a nucleic acid, such as a nuclear DNA.

Conversely, an off-target analyte is an analyte that normally would be analyzed using an enzymatic reaction, but which is not the target analyte of interest, such that both the analyte of interest and the off-target analyte are analyzed, thereby decreasing accuracy and reliability of results. An off-target analyte is an analyte that it would be preferable not to analyze. Therefore, the embodiments provided herein relate to methods and compositions that eliminate, reduce, or inhibit off-target analyte analysis.

Target nucleic acids can include a sample in which the average size of a nucleic acid in the sample is less than, greater than, or equal to about 2 kb, 1 kb, 500 bp, 400 bp, 200 bp, 100 bp, 50 bp, or a range between any two of the foregoing sizes. In some embodiments, the average size of a nucleic acid in the sample is less than, greater than, or equal to about 2000 nucleotides, 1000 nucleotides, 500 nucleotides, 400 nucleotides, 200 nucleotides, 100 nucleotides, 50 nucleotides, or a range between any two of the foregoing sizes.

As used herein, the term "reagent" describes an agent or a mixture of two or more agents useful for reacting with, interacting with, diluting, or adding to a sample, and may include agents used in assays described herein, including agents for lysis, nucleic acid analysis, nucleic acid amplification reactions, protein analysis, tagmentation reactions, ATAC-seq, CPT-seq, or SCI-seq reactions, or other assays. Thus, reagents may include, for example, buffers, chemicals, enzymes, polymerase, primers having a size of less than 50 base pairs, template nucleic acids, nucleotides, labels, dyes, or nucleases. In some embodiments, the reagent includes lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus, purification results in an "enrichment," for example, an increase in the amount of a desirable protein and/or nucleic acid sequence in the sample.

Advantages of the methods and compositions described herein may include, for example, specific targeting DNA of interest through open chromatin sequencing (ATAC-seq), reducing, inhibiting, or eliminating undesired mitochondrial sequencing reads from the analysis, reducing or eliminating the need to separate undesired targets providing less burden on separation methods, and reducing costs as undesired information is not collected and analyzed.

The methods can also be combined by controlling reactivity and selectivity of the enzyme. The compositions and methods described herein control activity and specificity of enzymes by blocking specific targets. As one of skill in the art will appreciate, similar principles can be also applied to assays related to DNA, proteins, RNA, or any analyte of interest, or a combination of analytes.

Embodiments of the systems and methods provided herein may be used in conjunction with a droplet partitioning system for use in isolating a sample within a droplet. As used herein, the term "partitioning" or "partitioned" refers to separating a sample into a plurality of portions, or "partitions." Partitions can be solid or fluid. In some embodiments, a partition is a solid partition, e.g., a micro channel. In some embodiments, a partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that the contents of one droplet does not diffuse into adjacent droplets. For example, partitioning may be performed using a droplet generator (e.g., BioRad systems, Dolomite Microfluidics systems, Micronit Microfluidics Systems, water-in-oil microfluidic devices, 10X Genomics systems, or any other suitable droplet partitioning system), to separately partition, isolate, and/or analyze a nucleic acid of interest.

Embodiments of the systems and methods provided herein include kits, containing transposition reagents and a first probe complementary to a first tag and a second probe complementary to a second tag, wherein the first and second probes are immobilized on a solid support. In some embodiments, the first probe and the second probe comprise a barcode. In some embodiments, the first probe and second probe is a polyT probe. In some embodiments, the solid support is an etched surface, a well, an array, a flow-cell device, a microfluidic channel, a bead, a magnetic bead, a column, a droplet, or a microparticle.

EXAMPLES

Example 1—Reducing Mitochondrial DNA Reads

The following example demonstrates an embodiment of reducing mtDNA reads using ATAC-seq.

A sample was obtained having both nuclear DNA and mtDNA. The sample was separated into various aliquots, and each aliquot was contacted with Hoechst 33258 dye in various concentrations, including 8 µM, 80 µM, and 800 µM. Each aliquot was then subjected to transposition and ATAC-seq, and the DNA reads were analyzed.

Figure 2A:
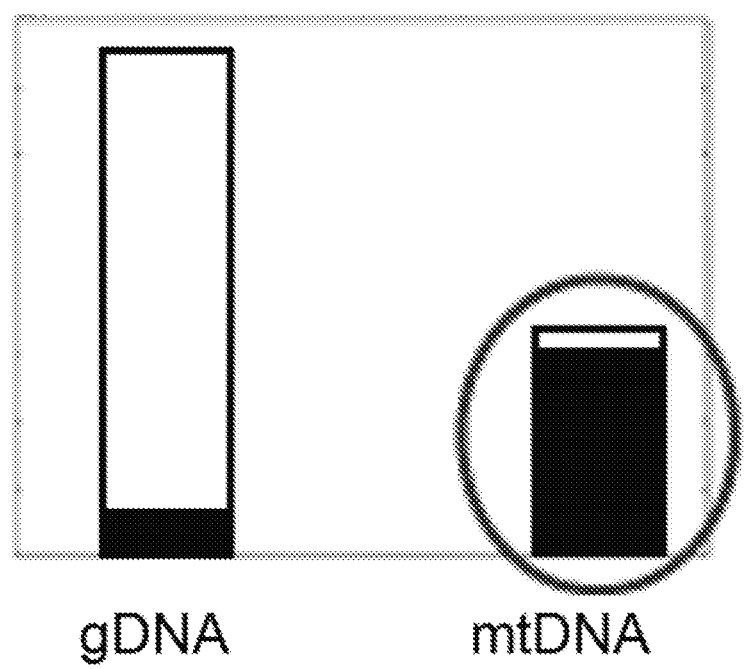
FIGS. 2A-2C depicts bar charts showing increasing amounts of Hoechst dye reduces mtDNA reads in transposition experiments, thereby eliminating or reducing undesirable mtDNA reads. From left to right, the concentration of Hoechst dye is 8 µM (FIG. 2A), 80 µM (FIG. 2B), and 800 µM (FIG. 2C).
Figure 2B:
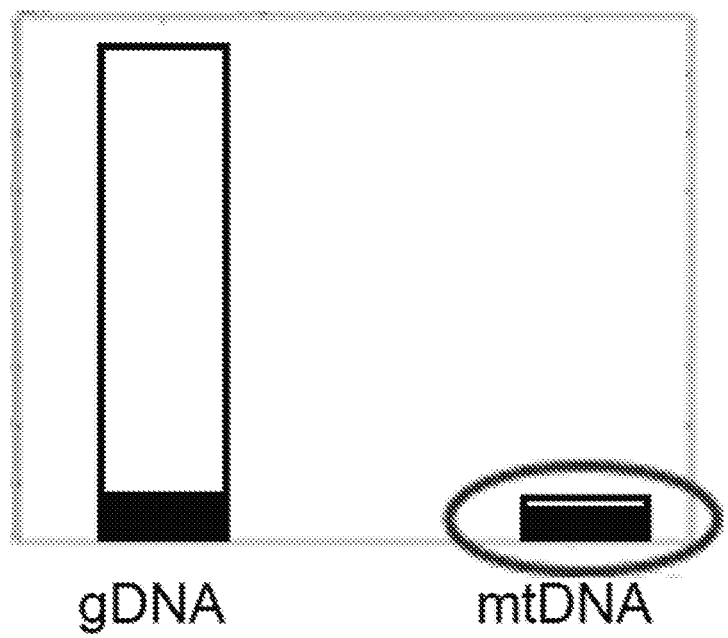
Figure 2C:
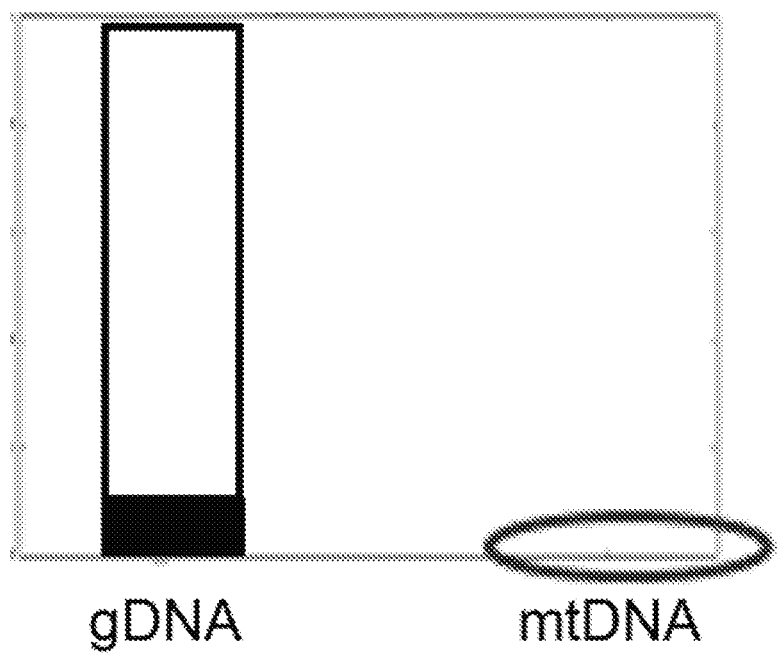

As shown in FIGS. 2A-2C, Hoechst dye selectively stained mtDNA, preventing transposition into mtDNA, but allowing transposition of nuclear DNA. Table 1 summarizes the resulting reads shown in FIGS. 2A-2C. Increasing concentrations of Hoechst dye resulted in decreasing mtDNA reads using ATAC-seq. The methods and compositions may be used for bulk ATAC-seq or single cell ATAC-seq to inhibit, reduce, or eliminate undesired mtDNA sequencing reads.

TABLE 1

| Concentration of Hoechst (µM) | 8 | 80 | 800 |
|---|---|---|---|
| % Mapped to gDNA (nuclear) | 68% | 89% | 100% |
| % Mapped to mtDNA | 32% | 11% | 0% |

In addition to performing transposition and ATAC-seq, the samples were also stained. The samples were stained with DAPI, and staining of mtDNA took place but not of actively transcribed (ATAC) regions of nuclear DNA. DAPI stained DNA, but not at certain locations. RNA is transcribed at locations where DAPI does not stain. The differential staining of mtDNA and not actively transcribed regions of nuclear DNA effectively inhibited transposition into mtDNA, and thereby improved efficiency of ATAC-seq of nuclear DNA without undesirable off-target transposition.

Example 2—Efficiency of Various DNA-Binding Molecules

The following example demonstrates an embodiment of reducing mtDNA reads using ATAC-seq by using various DNA-binding molecules.

Figure 3A:
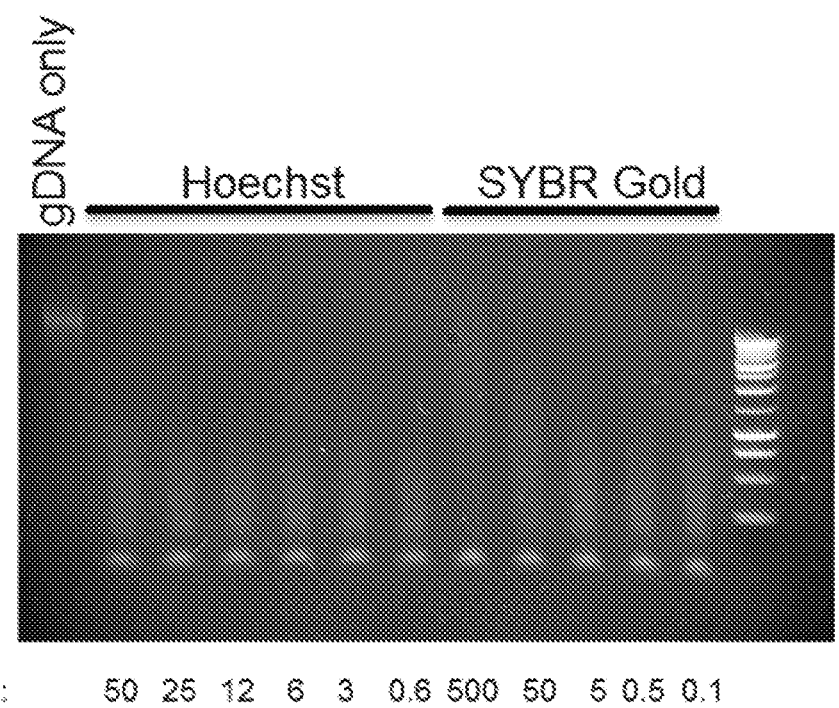
FIGS. 3A-3C depict DNA gels showing transposition efficiency of various DNA staining dyes.
Figure 3B:
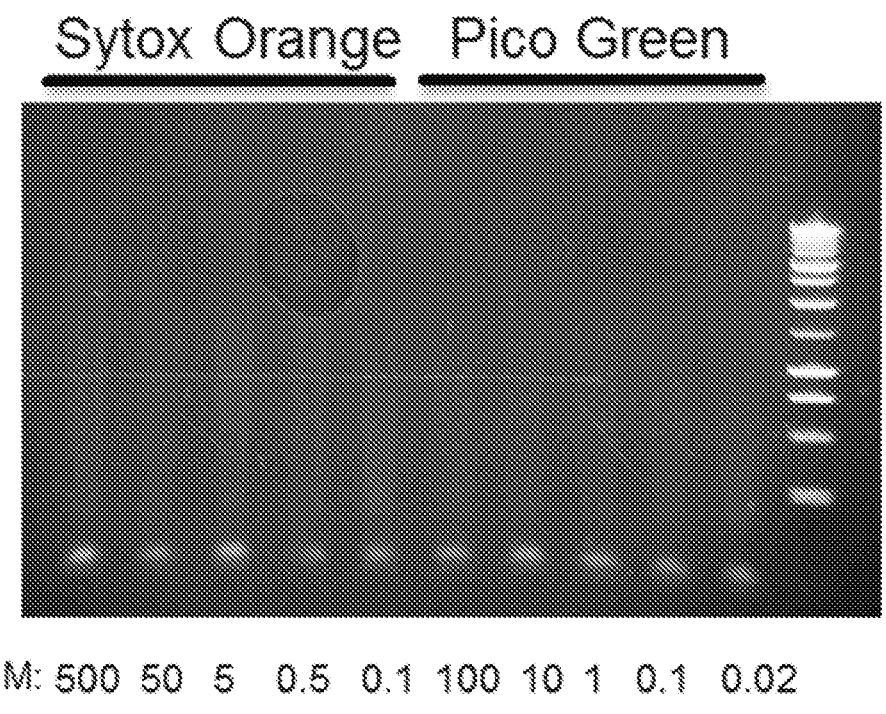
Figure 3C:
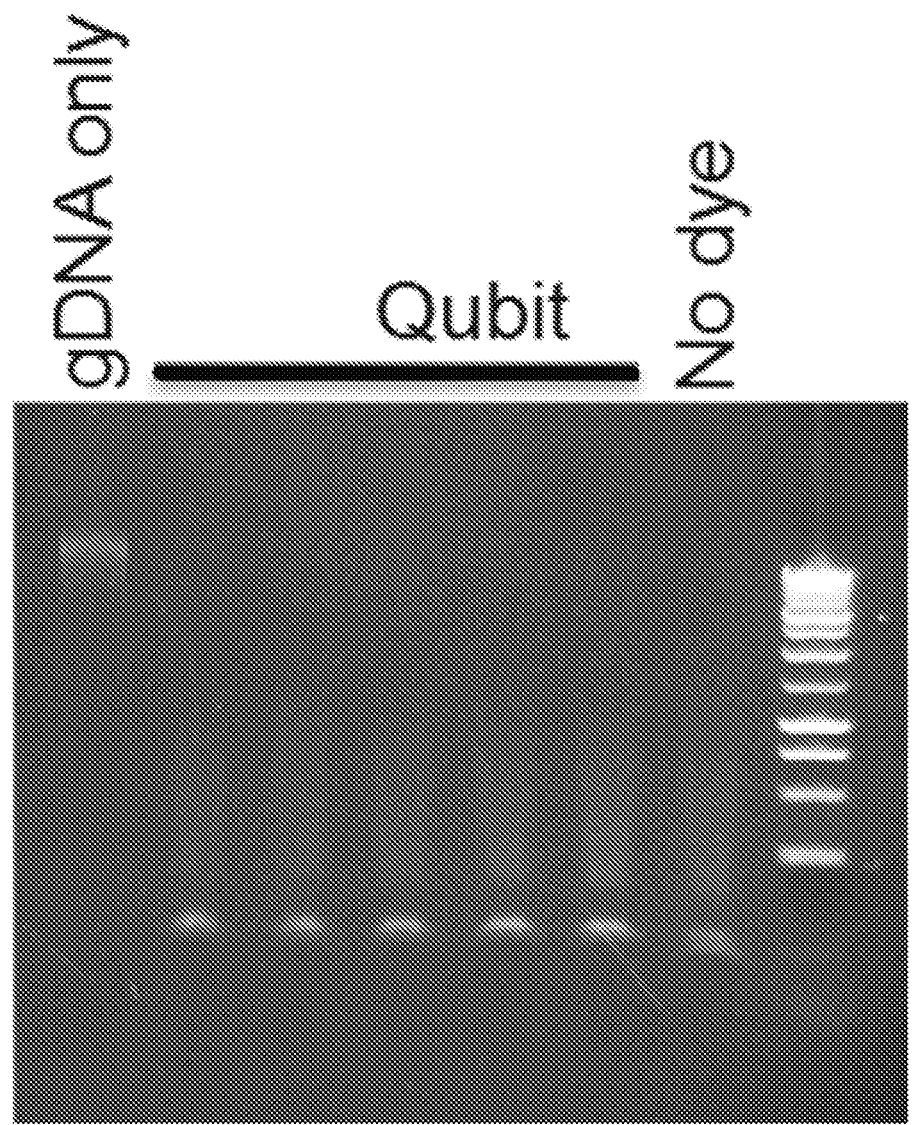

A sample was obtained having both nuclear DNA and mtDNA. The sample was separated into various aliquots, and each aliquot was contacted with a different dye in various concentrations. Five different dyes were used, including Hoechst (at concentrations of 50 µM, 25 µM, 12 µM, 6 µM, 3 µM, and 0.6 µM), SYBR Gold (at concentrations of 500 µM, 50 µM, 5 µM, 0.5 µM and 0.1 µM) Sytox Orange (at concentrations of 500 µM, 50 µM, 5 µM, 0.5 µM, and 0.1 µM), PicoGreen (at concentrations of 100 µM, 10 µM, 1 µM, 0.1 µM, and 0.02 µM), and Qubit (at concentrations of 100 µM, 10 µM, 1 µM, 0.1 µM, and 0.02 µMM) as shown in FIGS. 3A-3C. Another aliquot was prepared that was not exposed to any dye. Each aliquot was then subjected to Nextera transposition and products were visualized on a gel. FIG. 3A depicts the gel for Hoechst and SYBR Gold. FIG. 3B depicts the gel for Sytox Orange and PicoGreen, and FIG. 3C depicts the gel for Qubit and no dye. High molecular weight DNA products are indicative of inefficient transposition. Inhibition is observed for SYBR Gold and Sytox Orange at greater than 100 µM concentrations.

Figure 4:
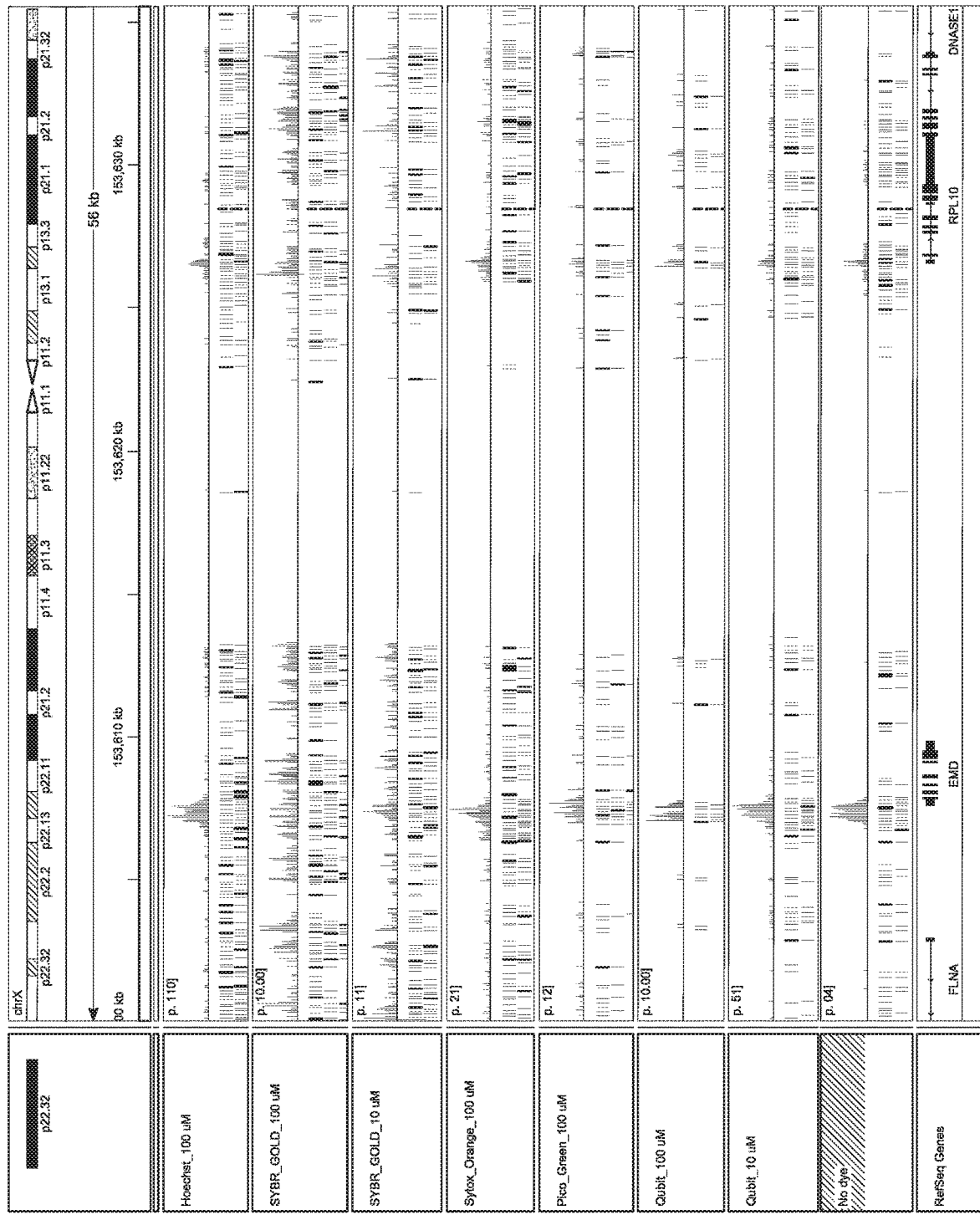
FIG. 4 depicts results of various tested dyes, including Hoechst (100 µM), SYBR Gold (at 100 µM and 10 µM), Sytox Orange (at 100 µM), Pico Green (at 100 µM), Qubit (at 100 µM or 10 µM) and no dye. The results indicate that only select dyes are suitable for reducing or eliminating secondary DNA sequencing reads.
Figure 5:
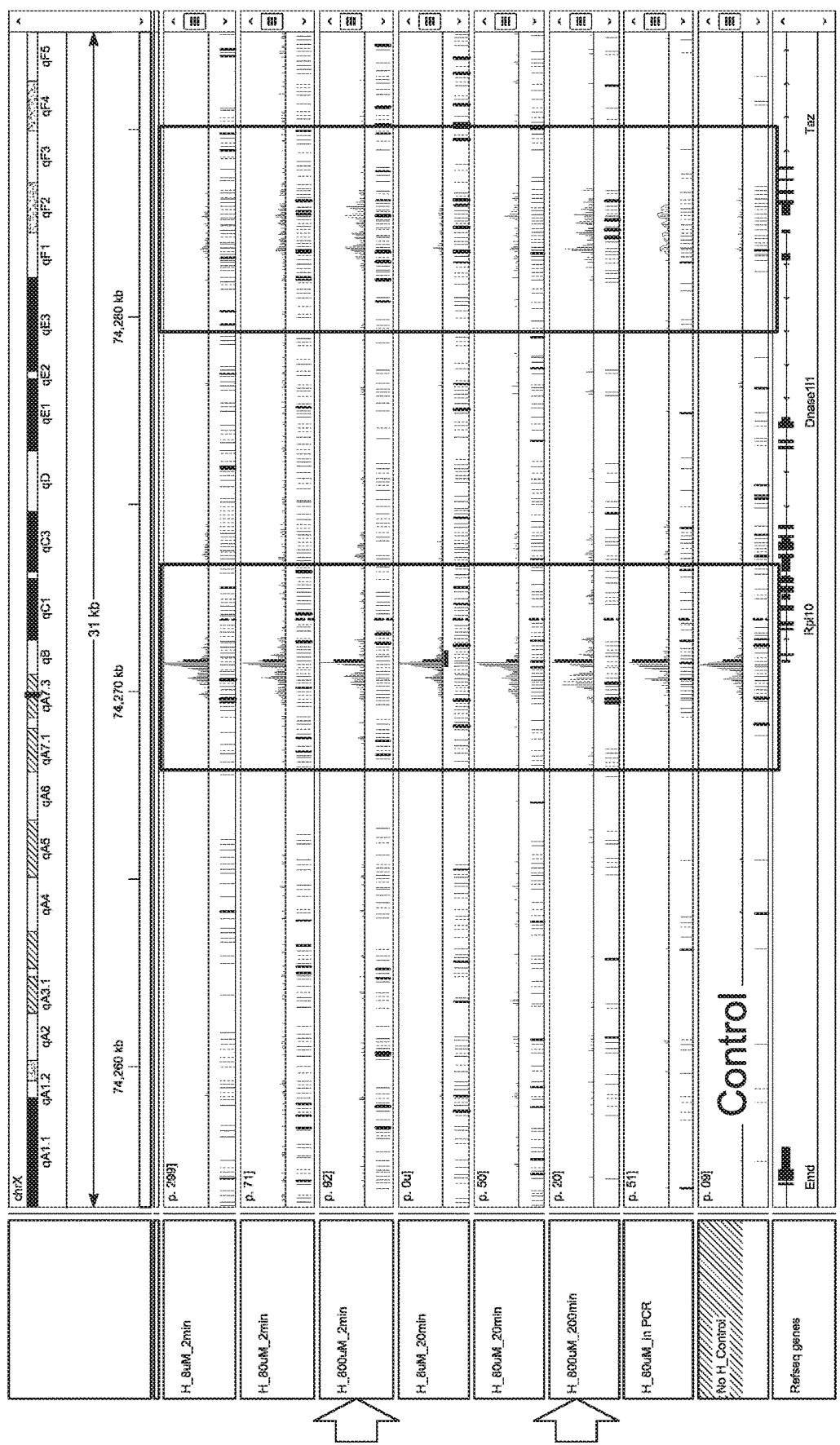
FIG. 5 depicts results of Hoechst staining at 8 µM, 80 µM, and 800 µM for various amounts of time (2 minutes or 20 minutes).

Each aliquot was subjected to transposition and the DNA reads were analyzed, as shown in FIGS. 4 and 5. As shown in FIG. 4, Hoechst 33258 does not alter the ATAC-seq profiles (nucleosome positioning) and reduces mitochondrial DNA reads (as shown also in FIGS. 2A-2C). Hoechst allows relatively unbiased ATAC-seq profiling while not changing nucleosome positioning. Some dyes, such as SYBR Gold, bind to DNA but affected nucleosome positioning (ATAC-seq) compared to the no dye control.

As shown in FIG. 5, specific blocking of mtDNA increased the specificity of nuclear DNA sequencing. These results demonstrate that intercalating DNA binding molecules can be used to control enzymatic transposition activity of DNA.

This approach can be applied more generally in which specific stains, or binding molecules in general, can be brought to certain targets using well-known affinity tags including antibody conjugates and DNA hybridization probes to block undesired enzymatic activity. Alternatively, specific affinity tags ("blockers") can be used to bring enzymes to specific targets. Such applications may include blocking off-target activity of CRISPR enzymes.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of sequencing a nucleic acid, comprising: contacting a sample with a DNA-binding molecule comprising a DNA dye; contacting the sample with an insertional enzyme complex to produce tagged nucleic acid fragments, wherein the insertional enzyme complex is inhibited by the DNA-binding molecule; and sequencing the tagged nucleic acid fragments to produce sequence reads; wherein the method inhibits, reduces, or eliminates secondary sequencing reads; and wherein the sample comprises primary nucleic acids and secondary nucleic acids, and wherein the DNA-binding molecule preferentially binds secondary nucleic acids over primary nucleic acids.

2. The method of claim 1, wherein the sample is a population of cells, a single cell, a population of cell nuclei, or a single cell nucleus.

3. The method of claim 1, wherein the primary nucleic acids comprise nuclear DNA.

4. The method of claim 1, wherein the secondary nucleic acids comprise mitochondrial DNA (mtDNA) or extrachromosomal DNA.

5. The method of claim 1, wherein the insertional enzyme complex is a transposome comprising a transposase.

6. The method of claim 1, wherein sequencing is performed by assay for transposase-accessible chromatin sequencing (ATAC-seq) or by whole genome sequencing.

7. The method of claim 1, wherein the DNA dye comprises Hoechst dye, SYBR Gold, Sytox Orange, Pico Green, or Qubit.

8. The method of claim 1, wherein the dye does not alter nucleosome positioning.

9. The method of claim 7, wherein the DNA dye comprises Hoescht dye.

10. The method of claim 8, wherein Hoescht dye is used at a concentration of between 8 μM and 800 μM.

11. The method of claim 9, wherein the Hoescht dye is used at a concentration of 800 μM.

12. The method of claim 7, wherein the DNA dye comprises SYBR Gold or Sytox Orange.

13. The method of claim 12, wherein the concentration of the DNA dye is greater than 100 μM.

14. The method of claim 1, wherein the DNA dye is 4',6-diamidino-2-phenylindole (DAPI).

15. The method of claim 6, wherein ATAC-seq comprises bulk ATAC-seq or single cell ATAC-seq.

16. The method of claim 5, wherein the transposase is selected from the group consisting of Tn5 transposase, Sleeping Beauty transposase, *Vibrio harveyi* transposase, or an active mutant thereof.

17. The method of claim 5, wherein the transposon comprises a transposon end sequence, wherein the transposon end sequence is a mosaic end sequence.

18. The method of claim 1, wherein the nucleic acid binding molecule preferentially binds to a specific DNA sequence or sequences.

* * * * *

UNITED STATES PATENT AND TRADEMARK OFFICE
CERTIFICATE OF CORRECTION

Page 1 of 1

PATENT NO. : 12,297,565 B2
APPLICATION NO. : 17/250846
DATED : May 13, 2025
INVENTOR(S) : Frank J. Steemers, Dmitry K. Pokholok and Lena Christiansen It is certified that error appears in the above-identified patent and that said Letters Patent is hereby corrected as shown below:

In the Claims

In Column 22, Line 29, in Claim 9, delete "Hoescht" and insert -- Hoechst --.

In Column 22, Line 30, in Claim 10, delete "Hoescht" and insert -- Hoechst --.

In Column 22, Line 32, in Claim 11, delete "Hoescht" and insert -- Hoechst --.

Signed and Sealed this
Sixteenth Day of September, 2025

Coke Morgan Stewart
*Acting Director of the United States Patent and Trademark Office*

```
                            SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
tcgtcggcag cgtcagatgt gtataagaga cag                                    33

<210> SEQ ID NO 2
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 2
gtctcgtggg ctcggagatg tgtataagag acag                                   34

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
ctgtctctta tacacatct                                                    19

<210> SEQ ID NO 4
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 4
tcgtcggcag cgtc                                                         14

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
gtctcgtggg ctcgg                                                        15

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 6
```

```
agatgtgtat aagagacag                                              19

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
aatgatacgg cgaccaccga gauctacac                                   29

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 8
caagcagaag acggcatacg agat                                        24
```